US012582694B2

(12) United States Patent
Baker et al.

(10) Patent No.: US 12,582,694 B2
(45) Date of Patent: *Mar. 24, 2026

(54) COMPOUNDS AND METHODS FOR INHIBITING PROTOZOAN PARASITES

(71) Applicant: University of South Florida, Tampa, FL (US)

(72) Inventors: Bill J. Baker, Temple Terrace, FL (US); Nerida G. Wilson, Cottesloe (AU); John H. Adams, Tampa, FL (US); Matthew A. Knestrick, Washington, DC (US); Alison Elizabeth Roth, North Bethesda, MD (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 724 days.

This patent is subject to a terminal disclaimer.

(21) Appl. No.: 17/742,640

(22) Filed: May 12, 2022

(65) Prior Publication Data

US 2022/0273756 A1 Sep. 1, 2022

Related U.S. Application Data

(63) Continuation of application No. 16/725,182, filed on Dec. 23, 2019, now Pat. No. 11,331,367.

(60) Provisional application No. 62/785,952, filed on Dec. 28, 2018.

(51) Int. Cl.
*A61K 38/08* (2019.01)
*A61K 31/4706* (2006.01)
*A61P 33/06* (2006.01)

(52) U.S. Cl.
CPC .......... *A61K 38/08* (2013.01); *A61K 31/4706* (2013.01); *A61P 33/06* (2018.01)

(58) Field of Classification Search
CPC .......... A61K 38/08; A61P 33/06; Y02A 50/30
See application file for complete search history.

(56) References Cited

PUBLICATIONS

Tajuddeen and Van Heerden, Malar J (2019) 18:404 (Year: 2019).*
Wikipedia primaquine description, six pages, downloaded from the Internet May 24, 24. (Year: 2024).*
Knestrick et al., J. Nat. Prod., 2019, 82, 2354-2358 (Year: 2019).*
Strategies to Reduce Sodium Intake in the United States (2010) portion of p. 91 provided (Year: 2010).*
Oceanic Research Group, update Mar. 11, 2014, The Wonders of the Sea, SPONGES: They are Nothing Like Sponge Bob!, 3 pages, downloaded from the Internet https://www.oceanicresearch.org/education/wonders/sponges.html, Mar. 4, 2025 (Year: 2014).*
Bracegirdle et al, J. Nat. Prod. 2022, 85, 2454-2460 (Year: 2022).*
Yang et al., Bioorganic & Medicinal Chemistry Letters, vol. 26, Issue 8, Apr. 15, 2016, pp. 2084-2087 (Year: 2016).*
Appleton, David R., et al. "Kottamides A—D: Novel Bioactive Imidazolone-Containing Alkaloids from the New Zealand Ascidian Pycnoclavella k Ottae." The Journal of Organic Chemistry 67.15 (2002): 5402-5404.
Boot, Claudia M., et al. "Highly N-methylated linear peptides produced by an atypical sponge-derived *Acremonium* sp." Journal of natural products 69.1 (2006): 83-92.
Chatterjee, Jayanta, et al. "N-methylation of peptides: a new perspective in medicinal chemistry." Accounts of chemical research 41.10 (2008): 1331-1342.
Izumikawa, Miho, et al. "Isolation of two new terpeptin analogs—JBIR-81 and JBIR-82—from a seaweed-derived fungus, *Aspergillus* sp. SpD081030G1f1." The Journal of Antibiotics 63.7 (2010): 389-391.
Kagamizono, Terumi, et al. "Terpeptin, a novel mammalian cell cycle inhibitor, produced by Aspergillus terreus 95F-1." Tetrahedron letters 38.7 (1997): 1223-1226.
Lang, Gerhard, et al. "Pterulamides I—VI, Linear Peptides from a Malaysian Pterula sp." Journal of natural products 69.10 (2006): 1389-1393.
Leal, Miguel Costa, et al. "Trends in the discovery of new marine natural products from invertebrates over the last two decades-where and what are we bioprospecting ?." PLoS One 7.1 (2012): e30580.
Mehbub, Mohammad Ferdous, et al. "Marine sponge derived natural products between 2001 and 2010: trends and opportunities for discovery of bioactives." Marine drugs 12.8 (2014): 4539-4577.
Palermo, Jorge A., Patricia Blanch Flower, and Alicia M. Seldes. "Chondriamides A and B, new indolic metabolites from the red alga *Chondria* sp." Tetrahedron Letters 33.22 (1992): 3097-3100.
Shiomi, Kazuro, et al. "New antibiotics miyakamides produced by a fungus." The Journal of antibiotics 55.11 (2002): 952-961.
Soldatou, Sylvia and Baker, Bill J. "Cold-water marine natural products, 2006 to 2016." Natural product reports 34.6 (2017): 585-626.
Toske, Steven G., et al. "Aspergillamides A and B: modified cytotoxic tripeptides produced by a marine fungus of the genus Aspergillus." Tetrahedron 54.44 (1998): 13459-13466.

* cited by examiner

*Primary Examiner* — Joseph Fischer
(74) *Attorney, Agent, or Firm* — Husch Blackwell LLP

(57) ABSTRACT

Described herein are compounds, formulations, and methods for blocking sporozoite invasion and subsequent liver-stage parasite development of a protozoan parasite, such as *Plasmodium falciparum.*

4 Claims, 3 Drawing Sheets

COMPOUNDS AND METHODS FOR INHIBITING PROTOZOAN PARASITES

CROSS-REFERENCE TO RELATED APPLICATIONS

This application is a continuation of U.S. patent application Ser. No. 16/725,182, filed Dec. 23, 2019, which claims benefit of U.S. Provisional Patent Application No. 62/785, 952, filed Dec. 28, 2018, each of which is hereby incorporated herein by reference in its entirety.

STATEMENT REGARDING FEDERALLY SPONSORED RESEARCH OR DEVELOPMENT

This invention was made with government support ANT1043749, ANT0838776 and PLR1341339 awarded by the National Science Foundation. The Government has certain rights in the invention.

BACKGROUND

*Plasmodium falciparum* is a unicellular protozoan parasite of humans, and the deadliest species of *Plasmodium* that cause malaria in humans. It is transmitted through the bite of a female Anopheles mosquito. It is responsible for roughly 50% of all malaria cases. It causes the disease's most dangerous form called *falciparum* malaria. It is therefore regarded as the deadliest parasite in humans, causing 435, 000 deaths in 2017. It is also associated with the development of blood cancer (Burkitt's lymphoma) and is classified as Group 2A carcinogen.

SUMMARY

Described herein are compounds, formulations, and methods for blocking sporozoite invasion and subsequent liver-stage parasite development of a protozoan parasite, such as *Plasmodium falciparum*.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows blood-stage antimalarial, DHA, does not inhibit *P. falciparum* liver-stage development while friomaramide and primaquine (PQ) show >90% inhibition. Graph bars represent means with s.d. for biological replicates (n=2) and experimental replicates (n=3). FIG. 3B shows friomaramide is nontoxic towards primary human hepatocytes at a 10 μM concentration where the dotted line indicates mean hepatocyte nuclei counts for 0.1% DMSO control.

DETAILED DESCRIPTION

Figure 1:
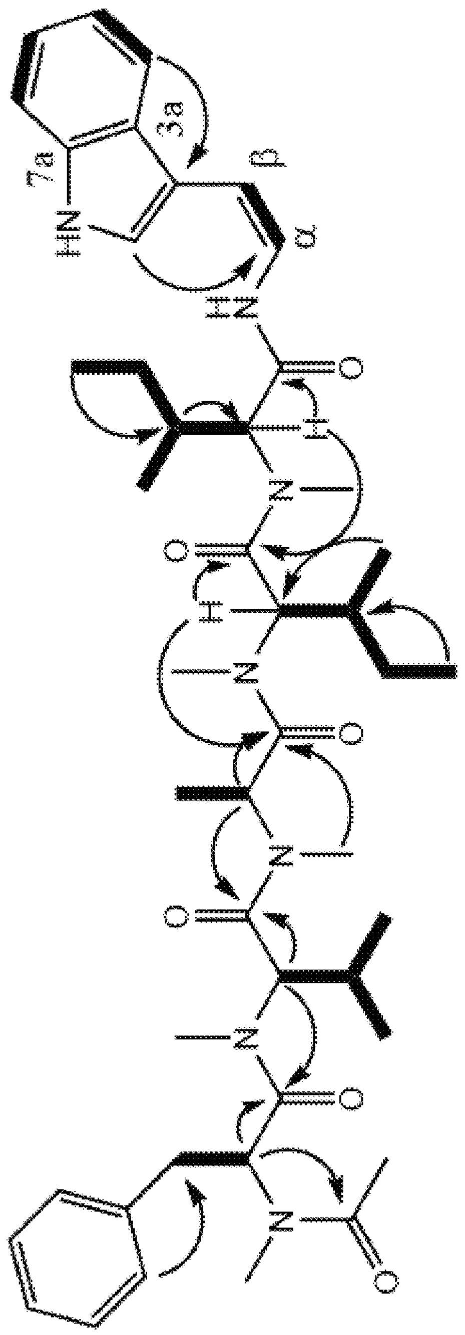
FIG. 1 is the chemical structure of friomaramide. Important COSY (bold) and HMBC (→) correlations are shown.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

As used in the specification and the appended claims, the singular forms "a," "an" and "the" include plural referents unless the context clearly dictates otherwise.

As used herein, the terms "optional" or "optionally" means that the subsequently described event or circumstance can or cannot occur, and that the description includes instances where said event or circumstance occurs and instances where it does not.

As used herein, "administering" refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "agent" refers to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "dose," "unit dose," or "dosage" refers to physically discrete units suitable for use in a subject, each unit containing a predetermined quantity of Compound (1) and/or a formulation thereof calculated to produce the desired response or responses in association with its administration.

As used herein, "effective amount" refers to the amount of a compound provided herein that is sufficient to effect beneficial or desired biological, emotional, medical, or clinical response of a cell, tissue, system, animal, or human. An effective amount can be administered in one or more administrations, applications, or dosages. The term cam also include within its scope amounts effective to enhance or restore to substantially normal physiological function. The "effective amount" can refer to the amount of the compounds (e.g. a compound (1)) or formulations thereof described herein that can allow for imaging of a cell, tissue, organ, or other portion of a subject to which the compound or formulation thereof is administered.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

As used herein, "substantially pure" means an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," refers to an amount (e.g. mass, volume, dosage, concentration, and/or time period) needed to achieve one or more desired result(s). For example, a therapeutically effective amount refers to an amount needed to achieve one or more therapeutic effects. In some embodiments, the effective amount can be anti-parasitic. In some embodiments, the effective amount can kill and/or inhibit a leishmanial parasite. In some embodiments, the effective amount can treat a leishmanial infection in a subject.

Described herein are compounds and formulations thereof that can block sporozoite invasion and subsequent liver-stage parasite development. In some embodiments, the compound can be compound (1), or a pharmaceutically acceptable salt thereof:

Compound (1)

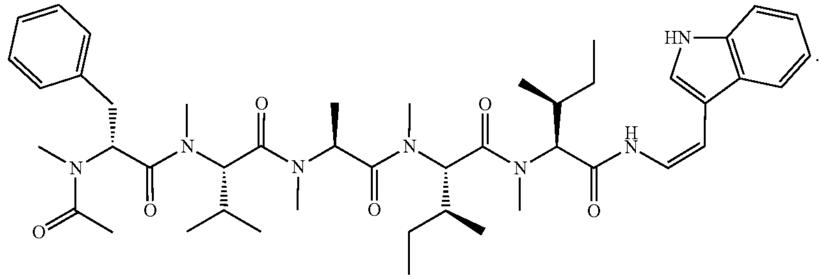

Compound (1) can be isolated from Antarctic sponge *Inflatella coelosphaeroides* according to the methods described in the Examples. After production, compound (1) can be extracted and purified according to techniques generally known in the art. Compound (1), or a pharmaceutically acceptable salt thereof, can also be synthesized using methods generally known in the art.

Compound (1), or a pharmaceutically acceptable salt thereof, can be included in a formulation, formulation that, in addition to the compound, can further include a suitable carrier. The carrier can be a pharmaceutically acceptable carrier. The formulation can be a pharmaceutical formulation. The compounds, salts and/or formulations thereof described herein can be administered to a subject. The subject can be infected with or be suspected of being infected with a leishmanial parasite. The subject can be a subject in need thereof. The compounds and formulations described herein can be administered by a suitable route, such as but not limited to oral, infusion, and intravenous. Other suitable routes are described elsewhere herein.

Compound (1), pharmaceutically acceptable salts thereof, and formulations thereof described herein can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the Compound (1), pharmaceutically acceptable salts thereof, and formulations thereof described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of Compound (1).

The formulation can be buffered to a pH of 3-8 for parenteral administration upon reconstitution. In some aspects, the pH of the formulation can be a pH of about 7.0-7.4 upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating Compound (1), or a pharmaceutically acceptable salt thereof, in the desired amount in the appropriate solvent or dispersion medium with one or more of the excipients listed above, as required, followed by filtered sterilization. Dispersions can be prepared by incorporating the Compound (1), or a pharmaceutically acceptable salt thereof, into a sterile vehicle which contains the basic dispersion medium and the required other ingredients from those listed above. Sterile powders for the preparation of sterile injectable solutions can be prepared by vacuum-drying and freeze-drying techniques, which yields a powder of the Compound (1), or a pharmaceutically acceptable salt thereof, with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of Compound (1), or a pharmaceutically acceptable salt thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, and use of nanotechnology including nanoformulations for parenteral administration can also contain one or more excipients, such as dispersing agents, wetting agents, and suspending agents.

Compound (1), or a pharmaceutically acceptable salt thereof, can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, Compound (1), or a pharmaceutically acceptable salt thereof, can be administered as a liquid formulation, such as a solution or suspension, a semi-solid formulation, such as a lotion or ointment, or a solid formulation. In some embodiments, Compound (1), or a pharmaceutically acceptable salt thereof, can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing Compound (1), or a pharmaceutically acceptable salt thereof, are also described herein. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing Compound (1), or a pharmaceutically acceptable salt thereof, are also described herein. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing Compound (1), or a pharmaceutically acceptable salt thereof, and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing Compound (1), or a pharmaceutically acceptable salt thereof, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include Compound (1), or a pharmaceutically acceptable salt thereof. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Compound (1), or a pharmaceutically acceptable salt thereof, can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing Compound (1), or a pharmaceutically acceptable salt thereof, can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing Compound (1), or a pharmaceutically acceptable salt thereof, can be prepared using one or more pharmaceutically acceptable excipients, including diluents, preservatives, binders, lubricants, disintegrators, swelling agents, fillers, stabilizers, and combinations thereof.

Delayed release dosage formulations containing Compound (1) can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing Compound (1), or a pharmaceutically acceptable salt thereof, can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

In use, Compound (1), or a pharmaceutically acceptable salt thereof, and formulations thereof described herein can be administered to a subject. In some embodiments, the subject is infected with or is suspected of being infected with a protozoan parasite, such as *Plasmodium falciparum*. Compound (1), a pharmaceutically acceptable salt thereof, or formulation thereof described herein can be co-administered or be a co-therapy with another active agent or ingredient that can be included in the formulation or provided in a dosage form separate from the Compound (1), a pharmaceutically acceptable salt thereof, or formulation thereof.

The amount of Compound (1), a pharmaceutically acceptable salt thereof, or formulation thereof can range from about 0.01 μg/kg to up to about 1000 mg/kg or more, depending on the factors mentioned elsewhere herein. In certain embodiments, the amount can range from 0.01 μg/kg up to about 500 mg/kg, or 1 μg/kg up to about 500 mg/kg, 5 μg/kg up to about 500 mg/kg, 0.01 μg/kg up to about 100 mg/kg, or 1 μg/kg up to about 100 mg/kg, 5 μg/kg up to about 100 mg/kg.

Administration of Compound (1), a pharmaceutically acceptable salt thereof, or formulation thereof can be systemic or localized. The Compound (1), a pharmaceutically acceptable salt thereof, or formulation thereof can be administered to the subject in need thereof one or more times per hour or day. In embodiments, the Compound (1), a pharmaceutically acceptable salt thereof, or formulation thereof can be administered once daily. In other embodiments, Compound (1), a pharmaceutically acceptable salt thereof, or formulation thereof can be administered can be administered 1 (q.d.), 2 (b.i.d.), 3 (t.i.d), 4 (q.i.d.), or more times daily. In some embodiments, when administered, an effective amount of Compound (1), a pharmaceutically acceptable salt thereof, or formulation thereof can be administered to the subject in need thereof. Compound (1) or formulation thereof can be administered one or more times per week. In some embodiments, Compound (1), a pharmaceutically acceptable salt thereof, or formulation thereof can be administered 1, 2, 3, 4, 5, 6 or 7 days per week. In some embodiments, Compound (1), a pharmaceutically acceptable salt thereof, or formulation thereof can be administered 1, 2, 3, 4, 5, 6, 7, 8, 9, 10, 11, 12, or more times per month. In some embodiments, Compound (1), a pharmaceutically acceptable salt thereof, or formulation thereof can be administered 1, 2, 3, 4, 5, 6, 7, 8, 9, 10, 11, 12, 13, 14, 15, 16, 17, 18, or more time per year.

In some embodiments, Compound (1), a pharmaceutically acceptable salt thereof, or formulation thereof can be administered in a dosage form. The amount or effective amount of Compound (1), a pharmaceutically acceptable salt thereof, or formulation thereof can be divided into multiple dosage forms. For example, the effective amount can be split into two dosage forms and the one dosage forms can be administered, for example, in the morning, and the second dosage form can be administered in the evening. Although the effective amount can be given over two or more doses, in one day, the subject can receives the effective amount when the total amount administered across all the doses is considered. The dosages can range from about 0.01 μg/kg to up to about 1000 mg/kg or more, depending on the factors mentioned above. In certain embodiments, the dosage can range from 0.01 μg/kg up to about 500 mg/kg, or 1 μg/kg up to about 500 mg/kg, 5 μg/kg up to about 500 mg/kg, 0.01 μg/kg up to about 100 mg/kg, or 1 μg/kg up to about 100 mg/kg, 5 μg/kg up to about 100 mg/kg.

EXAMPLES

Example 1: Friomaramide, a Highly Modified Linear Hexapeptide from an Antarctic Sponge, Inhibits Liver Stage *Plasmodium falciparum*

The world's oceans, covering ~70% of the Earth's surface, represent the largest source of biological and chemical diversity on the planet (Haefner, B. Drug Discov. Today 2003, 8, 536-544). Among marine animals, invertebrates are the most taxonomically diverse, together representing 60% of marine animal life (Ausubel, J. H., et al. Census of Marine Life: Washington, D.C., 2010; Leal, M. C., et al. PLoS One 2012, 7, 1-15). Many of these invertebrates are sessile and soft-bodied and often rely on chemical defenses to deter predators (von Salm, J. L., et al. In: Marine Chemical Ecology, Puglisi, M. P.; Becerro, M. A., Eds., CRC Press, Boca Raton, FL, Ch. 2), making them promising sources of unique, bioactive chemistry. Antarctica's geographic and biological isolation is largely attributed to the Antarctic Circumpolar Current (ACC). Though relatively slow, it is the largest ocean current in the world and circulates clockwise around the continent (McClintock, J. B., et al. Integr. Comp. Biol. 2005, 45, 359-368), transporting nutrient rich deep water throughout the waters surrounding Antarctica while isolating it from northern oceans (McClintock, J. B., et al. Integr. Comp. Biol. 2010, 50, 967-980). Antarctica has a highly productive marine ecosystem (Clarke, A., et al. Philos. Trans. R. Soc. B 2007, 362, 149-166). The shallow-water communities are dominated by large macroalgal forests and rich assemblages of sponges, soft corals, bryozoans, hydroids, and ascidians (McClintock, J. B., et al. Integr. Comp. Biol. 2010, 50, 967-980). Many of these soft-bodied invertebrates experience intense predation, so the chemical diversity of Antarctic marine invertebrates is high (Soldatou, S., et al. Nat. Prod. Rep. 2017, 34, 585-626).

Natural products from sponges are known for their chemical novelty and potent, broad spectrum biological activity (Mehbub, M., et al. Drugs 2014, 12, 4539-4577). Sponges are morphologically and taxonomically diverse, are widespread in the world's oceans, and play important ecological roles in benthic ecosystems (Hooper, J. N. A., et al. In: Systema Porifera; Hooper, J. N. A., Van Soest, R. W. M., Eds.; Springer US: Boston, MA, 2002; pp 1-7). Chemically, sponges predominate natural products drug discovery. Of all marine invertebrate natural products reported from 1990-2010, nearly half were reported from phylum Porifera, with approximately 250 new natural products reported on average every year (Leal, M. C., et al. PLoS One 2012, 7, 1-15). In the last ten years, more new sponge natural products (2500 total) have been reported than any other marine invertebrate phylum (Mehbub, M., et al. Drugs 2014, 12, 4539-4577). Sponge natural products therefore remain a promising source of new and unique chemical diversity.

To access the wealth of chemical diversity from the Southern Ocean, an extensive collection of marine invertebrates, and in particular sponges, were obtained. Herein is presented the study of the Antarctic sponge *Inflatella coelosphaeroides* and the isolation and characterization of a new, highly modified linear peptide, friomaramide (1).

Friomaramide (1)

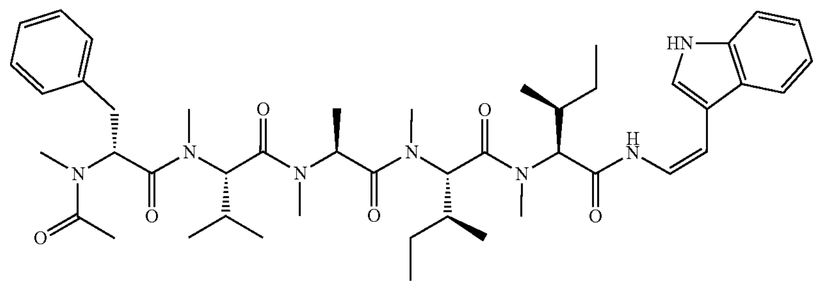

$C_{46}H_{67}N_7O_6$; HRESIMS m/z 814.5231 $[M+H]^+$ ($C_{46}H_{68}N_7O_6$, calculated 814.5231), m/z 836.5051 $[M+Na]^+$ ($C_{46}H_{67}N_7O_6Na$, calculated 836.5050); UV (MeOH) $\lambda_{max}$ (log ε) 230 (2.81); $[\alpha]_D^{25}$=−150 (c 0.1, MeOH); IR (thin film) 3450, 3050, 2980, 2960, 1700, 1680, 1635, 1500, 1240 $cm^{-1}$; $^1H$ NMR (800 MHz, $CD_3OD$); $^{13}C$ NMR (200 MHz, $CD_3OD$).

*Inflatella coelosphaeroides* was collected via trawling in the northern reaches of the Scotia Arc in the Southern Ocean. Sponges were freeze dried and extracted with dichloromethane:methanol (1:1). The extract was mounted on silica gel and subjected to normal phase MPLC. Further purification of the ethyl acetate methanol (3:1) eluting fractions was accomplished with reversed phase HPLC eluted with acetonitrile, yielding a highly N-methylated peptide.

Friomaramide (1) was determined to have a molecular formula of $C_{46}H_{67}N_7O_6$ based on high-resolution electrospray ionization mass spectrum (HRESIMS) (m/z 814.5231 [M+H]+, calculated 814.5231) and corroborated by the $^1H$ and $^{13}C$ NMR spectra. Evaluation of the $^1H$ and $^{13}C$ NMR spectra, as well as the correlations of each in the heteronuclear single quantum coherence (HSQC) spectrum, indicated the presence of five notable nitrogen-bearing methyl groups, multiple aromatic signals, and six ester/amide-type carbonyls, as well as two olefinic, eight methine, three methylene, and eight aliphatic/acyl methyl carbons (Table 1).

The structure of friomaramide (1) was determined spectroscopically. Among the evident intact amino acid residues, heteronuclear multiple bond correlation (HMBC) data correlated each α-methine proton ($\delta_H$ 5.09-5.34) to two carbonyls ($\delta_C$ 172.7-175.8) and a singlet N-methyl ($\delta_H$ 2.78-3.01). These correlations suggested that the molecule was an N-methylated peptide, with each α-position methine displaying correlations to the carbonyl of its own amino acid and of the subsequent amino acid in the peptide chain. Interestingly, all of the intact amino acids displayed nitrogen methylation, indicated by the number of N-methyl signals corresponding to the number of amide carbonyl groups. With this knowledge, the HMBC and $^1$H-$^1$H correlation spectroscopy (COSY) spectra were used to construct each amino acid within the molecule (FIG. 1). Alanine, phenylalanine, valine, and two isoleucine residues were identified.

Figure 2:
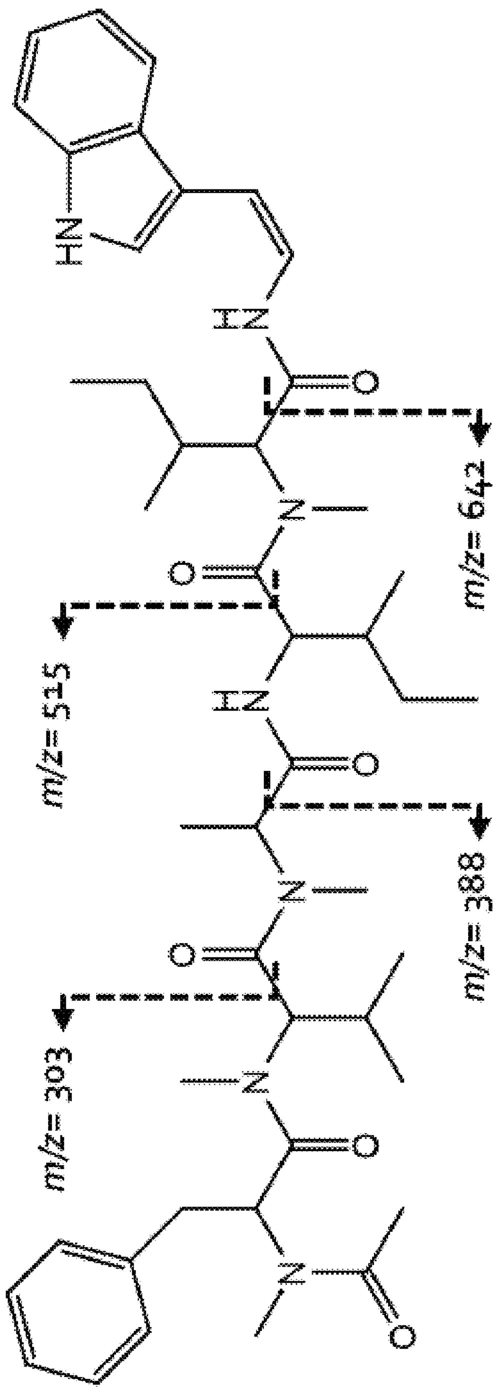
FIG. 2 shows HRESIMS fragmentation of friomaramide.

The sequence of five methylated amino acids was established using gHMBC correlations, supported by analysis of the HRESIMS fragmentation pattern (FIG. 2). In particular, the α-methine protons, which displayed correlations to the adjacent amide carbonyls, were critical to establishing the peptide sequence. The α-methine of Phe ($\delta_H$ 5.14) displayed an HMBC correlation to the Phe amide carbonyl ($\delta_C$ 175.1), but no other amino acid carbonyl, indicating it was the terminal amino acid. The α-methine proton of Val ($\delta_H$ 5.04) displayed correlations to both the Val ($\delta_C$ 172.7) and Phe carbonyls; the Ala α-methine ($\delta_H$ 5.17) displayed correlations to the Ala ($\delta_C$ 175.8) and Val carbonyls; the $Ile_1$ α-methine ($\delta_H$ 5.09) displayed correlations to the $Ile_1$ ($\delta_C$ 172.8) and the Ala carbonyls; and finally the α-methine of $Ile_2$ ($\delta_H$ 5.34) displayed correlations to the $Ile_2$ ($\delta_C$ 173.8) and the $Ile_1$ carbonyls. The sequence amino acids was thus established as Phe-Ala-Val-$Ile_1$-$Ile_2$.

TABLE 1

NMR data for friomaramide in MeOH-$d_4$

| Pos | $\delta_C$[b] | $\delta_H$(m, J(Hz))[a] | COSY | HMBC |
|---|---|---|---|---|
| Acetyl | | | | |
| CO | 173.9 | | | |
| Me | 23.4 | 1.92 (s, 3H) | | Ac-CO |
| Phenylalanine | | | | |
| CO | 175.1 | | | |
| α | 53.3 | 5.14 (t, 15.7, 1H) | β | N-Me, Ac-CO, Phe-CO |
| β | 40.2 | 2.90 (m, 1H) | α | 1, 2/6, Phe-CO |
| | | 3.05 (m, 1H) | | |
| 1 | 141.6 | | | |
| 2/6 | 129.5 | 7.28 (br m, 2H) | 3/5, 4 | 4 |
| 3/5 | 138.5 | 7.25 (br m, 2H) | 2/6, 4 | 1 |
| 4 | 139.2 | 7.23 (br m, 1H) | 2/6, 3/5 | 1 |
| N-Me | 32.6 | 2.86 (s, 3H) | α | |
| Valine | | | | |
| CO | 172.7 | | | |
| α | 62.9 | 5.04 (d, 11, 1H) | β | γ, γ', N-Me, Phe-CO, Val-CO |
| β | 29.8 | 2.21 (m, 1H) | α, γ, γ' | |
| γ | 12.2 | 0.80 (d, 7.3, 3H) | β | α, γ' |
| γ' | 16.4 | 0.83 (d, 7.3, 3H) | β | α, γ |
| N-Me | 34.6 | 2.78 (s, 3H) | | Val-CO |
| Alanine | | | | |
| CO | 175.8 | | | |
| α | 59.4 | 5.17 (m, 1H) | β | N-Me, Val-CO, Ala-CO |
| β | 15.7 | 1.20 (d, 7.0, 3H) | α | α, Ala-CO |
| N-Me | 32.8 | | | α, Ala-CO |
| $Isoleucine_1$ | | | | |
| CO | 172.8 | | | |
| A | 59.4 | 5.09 (d, 11, 1H) | β | β-Me, γ, N-Me, Ala, CO, $Ile_1$-CO |
| β | 35.7 | 1.98 (m, 1H) | α, β-Me, γ | |
| β-Me | 19.6 | 0.76 (d, 6.5, 3H) | β | α |
| γ | 26.7 | 1.29 (m, 2H) | δ | α |
| δ | 16.7 | 0.60 (d, 6.5, 3H) | γ | β |
| N-Me | 34.3 | 3.01 (s, 1H) | | α, $Ile_1$-CO |
| $Isoleucine_2$ | | | | |
| CO | 173.8 | | | |
| α | 61.2 | 5.34 (m, 1H) | β | β-Me, γ, |
| β | 35.8 | 2.10 (m, 1H) | α', β-Me, γ | δ |
| β-Me | 16.9 | 0.81 (d, 6.5, 3H) | β | α |
| γ | 26.7 | 1.16 (m, 2H) | δ | α |
| δ | 21.2 | 0.78 (d, 6.5, 3H) | γ | β |
| N-Me | 31.7 | 3.09 (s, 3H) | α, $Ile_2$-CO | |

TABLE 1-continued

| NMR data for friomaramide in MeOH-$d_4$ | | | | |
|---|---|---|---|---|
| Pos | $\delta_C$[b] | $\delta_H$(m, J(Hz))[a] | COSY | HMBC |
| Tryptenamine | | | | |
| 2 | 138.0 | 7.22 (s, 1H) | | 3, 3a, 7a |
| 3 | 109.9 | | | |
| 3a | 129.5 | | | |
| 4 | 128.7 | 7.60 (d, 7.8, 1H) | 5 | 3, 7a, 6 |
| 5 | 130.9 | 7.08 (t, 7.2, 1H) | 4, 6 | 3a, 7 |
| 6 | 132.3 | 7.15 (t, 7.2, 1H) | 5, 7 | 4, 7a |
| 7 | 121.9 | 7.36 (d, 7.8, 1H) | 6 | 3a, 5 |
| 7a | 138.5 | | | |
| α | 133.5 | 6.31 (d, 8.3, 1H) | α | 3, β |
| β | 129.3 | 6.59 (d, 8.2, 1H) | β | 2, 3a, α |

[a] $^1$H NMR spectrum recorded at 800 MHz, ppm (multiplicity, J (Hz), integration)
[b] $^{13}$C NMR spectrum recorded at 200 MHz The N-terminus of the peptide was determined to be acetylated, indicated by HMBC correlation between the α-methine proton of Phe ($\delta_H$ 5.14) and an acetyl carbonyl at $\delta_C$ 173.9. The C-terminus was composed of an eliminative decarboxylation tryptophan product, tryptenamine. COSY-coupled aromatic protons indicated the presence of an aromatic ring within the residue ($\delta_H$ 7.08-7.60). The chemical shift of C-3a ($\delta_C$ 129.5) and −7a ($\delta_C$ 138.5), as well as HMBC correlations of H-4 ($\delta_H$ 7.60) and −2 ($\delta_H$ 7.22) with C-3 ($\delta_C$ 109.9) and −7a, respectively, verified the fused aromatic ring system of tryptophan. The olefin comprising positions α ($\delta_C$ 133.5) and β ($\delta_C$ 129.3) were identified by HMBC correlations between $C_\alpha$ and $C_\beta$ with the H-3 and -2, respectively. The cis-orientation of the olefin was assigned on the basis of $J_{\alpha,\beta}$=8.2 Hz. Though only a week long-range correlation existed between tryptenamine and the rest of the peptide, the HRESIMS fragmentation (FIG. 2) supported its placement as the C-terminus of friomaramide (1).

Figures 3A, 3B:
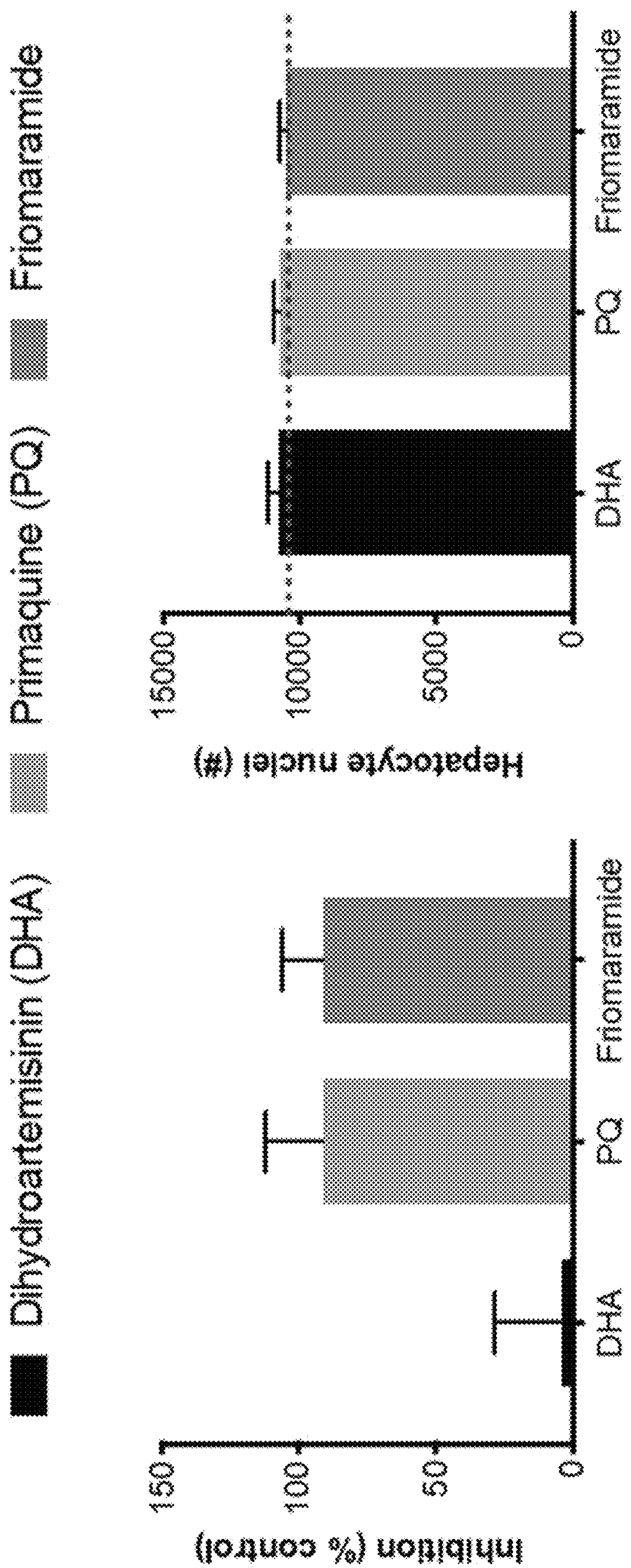
FIGS. 3A and 3B show friomaramide activity against *P. falciparum* liver-stage parasites and assessment of hepatocyte toxicity.

Bioactivity of friomaramide was evaluated for inhibition of *Plasmodium falciparum* liver-stage parasites and primary human hepatocyte (PHH) toxicity using an in vitro liver model. In brief, cryopreserved PHHs were seeded at $1.8\times10^4$ cells per well in a 384-well microplate. Freshly isolated *P. falciparum* sporozoites were inoculated at $2.0\times10^4$ per well with subsequent drug treatment at 10 μM. Media was changed daily with fresh addition of drug for 3 days until experiment fixation on day 6. Frioaramide showed 92%±14% (±standard deviation) inhibition of *P. falciparum* liver-stage growth which is highly comparable to primaquine, a known liver-stage acting antimalarial drug (FIG. 3A). Further, treatment with friomaramide elicited no toxic effects towards PHHs determined by quantification of fluorescently labeled hepatocyte nuclei indicating viable nuclei (FIG. 3B).

Friomaramide (1) brings a number of new structural features to light. Tryptenamine as an N-terminus to a small peptide is found only rarely, primarily among fungi, as in the terpeptins, which are prenylated tripeptides terminating in tryptenamine (Kagamizono, T., et al. Tetranderon Lett. 1997, 38, 1223-1226). From the marine environment, only compounds from an alga (Palermo, J. A., et al. Tetrahedron Lett. 1992, 33, 3097-3100) and a tunicate (Appleton, D. R., et al. J. Org. Chem. 2002, 67, 5402-540) have been found bearing tryptenamine, though in those two examples, the tryptenamine was not a terminus of a peptide chain. Friomaramide introduces a sponge source of this unusual amino acid derivative and, taken with the peptidic nature of the molecule, implicates host-associated fungi as the actual producer. Few fungal tryptenamine N-terminating peptides are fully N-methylated, though some small peptides lacking tryptenamine are as highly N-methylated as friomaramide (Lang, G., et al. J. Nat. Prod. 2006, 69, 1389-1393; Boot, C. M., et al. J. Nat. Prod. 2006, 69, 83-92). The tryptenamine-free peptides can be up to eight amino acids in length while those bearing tryptenamine are never larger than three amino acids. With five amino acids accompanying tryptenamine on friomaramide, it appears 1 may be a hybrid between the terpeptin (Kagamizono, T., et al. Tetranderon Lett. 1997, 38, 1223-1226)/miyakamide (Shiomi, K., et al. J. Antibio. 2002, 55, 952-961) type tripeptides, and pentapeptide pterulamide (Toske, S. G., et al. Tetrahedron 1998, 54, 13459-13466) or RHM octapeptide (Izumikawa, M., et al. J. Antibiot. 2010, 63, 389-391) type products. Acetylation on the C-terminus amino acid, as found in friomaramide is rare among fungal products. Peptide methylation is attractive in drug discovery, as non-methylated peptides have poor pharmacokinetic properties (short in vivo half-life, poor oral availability) (Chatterjee, J., et al. Acc. Chem. Res. 2008, 41, 1331-1342).

Friomaramide is a new, highly modified peptide. In the face of rising drug resistance, it is important to find new chemodiversity sources from natural products. Friomaramide was found to block sporozoite invasion and subsequent liver-stage parasite development showing similar inhibitory activity as the known liver-stage antimalarial drug primaquine. Structurally, friomaramide contains a number of unique and uncommon modifications for a small peptide. This chemical novelty and biological specificity substantiates efforts to continue to explore marine, cold-water organisms as potential sources of exciting natural products.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising Compound (1):

(1)

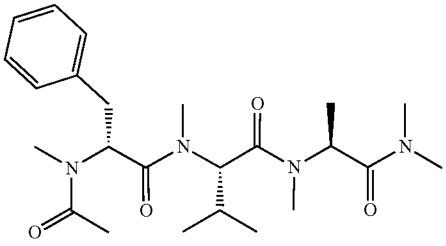

-continued

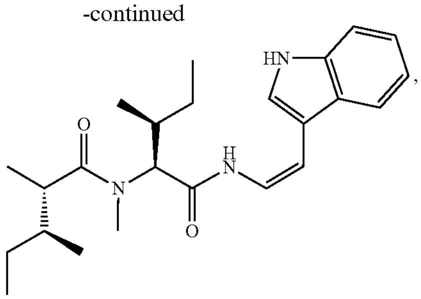

or a pharmaceutically acceptable salt thereof; and an antimalarial drug;

wherein the antimalarial drug is primaquine.

2. The composition of claim 1, wherein the composition comprises a pharmaceutical formulation.

3. The composition of claim 2, comprising one or more additional active agents.

4. A composition consisting of Compound (1):

(1)

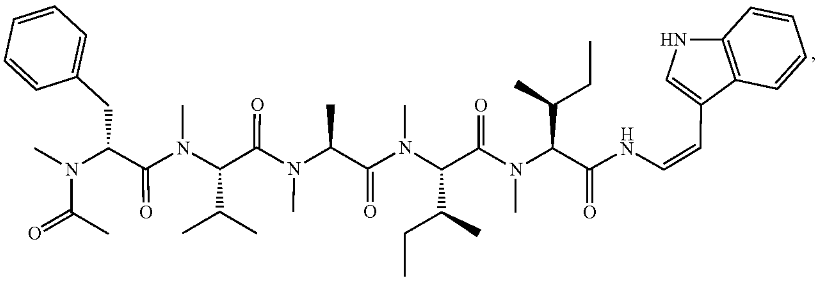

or a pharmaceutically acceptable salt thereof; and an antimalarial drug;

wherein the antimalarial drug is primaquine.

* * * * *